United States Patent
Slate et al.

(10) Patent No.: US 7,217,253 B2
(45) Date of Patent: *May 15, 2007

(54) SEQUENTIAL IMPULSE/DELIVERY FLUID MEDICAMENT INJECTOR

(75) Inventors: John B. Slate, San Diego, CA (US); Michael W. Burk, San Marcos, CA (US); Lanny A. Gorton, San Diego, CA (US)

(73) Assignee: Avant Medical Corp., San Diego, CA (US)

( * ) Notice: Subject to any disclaimer, the term of this patent is extended or adjusted under 35 U.S.C. 154(b) by 495 days.

This patent is subject to a terminal disclaimer.

(21) Appl. No.: 10/662,001

(22) Filed: Sep. 12, 2003

(65) Prior Publication Data

US 2004/0059286 A1  Mar. 25, 2004

Related U.S. Application Data

(63) Continuation-in-part of application No. 09/892,366, filed on Jun. 26, 2001, now Pat. No. 6,652,483.

(51) Int. Cl.
*A61M 5/30* (2006.01)
(52) U.S. Cl. .......................................... 604/68; 604/72
(58) Field of Classification Search ................. 604/68, 604/69, 70, 71, 72, 500
See application file for complete search history.

(56) References Cited

U.S. PATENT DOCUMENTS

| | | | |
|---|---|---|---|
| 3,605,745 A | 9/1971 | Hodosh | |
| 3,640,277 A | 2/1972 | Adelberg | |
| 4,059,107 A | 11/1977 | Iriguchi et al. | |
| 4,437,859 A | 3/1984 | Whitehouse et al. | |
| 5,298,023 A * | 3/1994 | Haber et al. | 604/90 |
| 5,911,703 A * | 6/1999 | Slate et al. | 604/68 |
| 6,102,896 A * | 8/2000 | Roser | 604/218 |
| 6,224,567 B1* | 5/2001 | Roser | 604/68 |
| 6,406,455 B1* | 6/2002 | Willis et al. | 604/68 |
| 6,645,170 B2* | 11/2003 | Landau | 604/68 |
| 6,652,483 B2* | 11/2003 | Slate et al. | 604/68 |
| 6,689,101 B2* | 2/2004 | Hjertman et al. | 604/131 |
| 2002/0055707 A1 | 5/2002 | Slate et al. | |
| 2004/0059286 A1 | 3/2004 | Slate et al. | |

OTHER PUBLICATIONS

Rayman, G., Walker R., Day, J.O., Diabetic Medicine, *Patient Experience with a Jet Injector*, Jan. 1, 1989, pp. 6: 274-276.

* cited by examiner

*Primary Examiner*—Kevin C. Sirmons
*Assistant Examiner*—Bhisma Mehta
(74) *Attorney, Agent, or Firm*—Nydegger & Associates

(57) ABSTRACT

A device and two-step sequential method for providing medication for injection and infusion by a jet injector includes a cassette which connects an injector system to a reservoir. The cassette forms a fluid pathway at an interface of a cassette lower body and a cassette upper body. The cassette also forms an impulse chamber with a nozzle leading therefrom. The fluid pathway interconnects the reservoir with the impulse chamber. The medication flows from the reservoir along the fluid pathway and into the impulse chamber. Force from an impulse generator drives the fluid medicament from the impulse chamber through the nozzle, out an orifice in a tip of the nozzle, and into the skin of a patient. To prevent the pressure waves generated by the jet injector from damaging a glass reservoir, the fluid pathway is formed with pressure attenuators.

19 Claims, 4 Drawing Sheets

SEQUENTIAL IMPULSE/DELIVERY FLUID MEDICAMENT INJECTOR

This application is a continuation-in-part of application Ser. No. 09/892,366 filed Jun. 26, 2001, now U.S. Pat. No. 6,652,483. The contents of application Ser. No. 09/892,366 are incorporated herein by reference.

FIELD OF THE INVENTION

The present invention pertains generally to medical devices. More particularly, the present invention pertains to medical devices for administering medication into the tissue of a patient. The present invention is particularly, but not exclusively, useful as a drug reservoir for a jet injection device.

BACKGROUND OF THE INVENTION

Subcutaneous and intramuscular delivery of fluid medicaments by injection are common in the medical arts. Some medications, such as insulin, must be given frequently by injection to an individual. In many cases, these injections are self-administered. In other cases, injections are given to a large number of persons, such as inoculations to prevent disease. In any event, it is desirable that the injections be accomplished easily.

Many patients dislike needle injections due to pain, fear, and nervousness over needles. Additionally, practice has indicated there are serious risks related to needle injections. For example, blood-borne pathogens, such as HIV and hepatitis, can be transmitted to health care workers by accidental needle-sticks. Specific environments which have an exceptionally high risk of accidental needle-sticks include emergency rooms, county hospitals, and sites of mass immunizations. Also, the disposal of used needles is a growing concern. This disposal presents a problem to individuals other than healthcare workers. Children, for example, may find used needles in the trash, putting them at risk of contracting infection. Discarded needles likewise pose a risk to waste disposal workers.

Injectable medications are typically supplied in glass vials sealed with an inert rubber stopper. To administer the fluid medicament, the user must transfer the fluid medicament from the vial to a fluid medicament delivery device, such as a syringe and needle, or a needleless jet injector syringe. Transferring the fluid medicament adds cost to administering injections in a hospital or clinic because of the labor expense. Immunizing large populations requires administering many injections per hour, hence transferring the fluid medicament presents a significant time constraint. For the patient who must self-administer fluid medicaments, such as a diabetic patient requiring several insulin injections a day, transferring the fluid medicament can be an inconvenience. Also, with each transfer, there is an opportunity for error in the amount of fluid medicament being transferred and administered.

In an effort to eliminate transferring a fluid medicament from a vial, pre-filled glass cartridges have been developed. These pre-filled cartridges are similar in design to a syringe. One end is closed and includes either a needle or an inert rubber stopper. If a needle is not integral, then a needle subassembly that penetrates the rubber stopper is attached prior to use. A movable rubber plunger closes the end opposite the needle. To administer the fluid medicament, the pre-filled cartridge is placed in a device consisting of a holder and a driver that meets the movable rubber plunger. The user depresses the plunger to dispense the medication.

An example of the use of pre-filled cartridges is in the treatment of diabetes with multiple daily injections of insulin. A pre-filled cartridge contains an amount of insulin sufficient for several days. Insulin is then delivered from the pre-filled cartridge using a pen injector, a pen shaped device for injecting the insulin. A disadvantage of pre-filled cartridges, however, is that they still require using a needle to penetrate the skin and deliver the medication to the target tissue.

In efforts to minimize the fears and risks associated with needle injections, several types of needle-free jet injectors have been developed. These devices penetrate the skin using a high velocity fluid jet, and deliver medication into the tissue of a patient. In order to accomplish this, a force is exerted on the liquid medication. Jet injectors, in general, contain a fluid medicament which has been transferred into a chamber having a small orifice at one end. A ram is accelerated using either a coil spring or a compressed gas energy source. The ram impacts a plunger, which in turn creates a high pressure impulse within the chamber. This pressure impulse ejects the fluid medicament through the orifice at high velocity, piercing the skin. The energy source continues to apply a force to the plunger, which quickly propels the medication through the opening in the skin, emptying the syringe in a fraction of a second.

Neither glass vials containing multiple doses of a medication nor pre-filled cartridges can be used with existing jet injectors. This is because a significant amount of impulse energy is transmitted from the energy source. Although not directly impacted, the glass walls of the cartridge do not have sufficient strength to withstand the large amplitude pressure waves that result when the ram impacts the plunger. To withstand the stresses caused by the high pressures, existing jet injector syringes have thick walls molded from an impact resistant plastic, such as polycarbonate.

It is known that the amount of the fluid medicament delivered by any injection system must be accurate. To this end, manual syringes are available in varying sizes, marked for ease of reading and accuracy of medication dose. Control mechanisms for jet injectors vary depending on whether a single use, single dose is contemplated. When multiple doses are to be administered, controlling the amount of fluid medicament dispensed becomes more complex.

In light of the above, it is an object of the present invention to provide a medicament reservoir for use with a jet injector system. Another object of the invention is to provide a jet injector assembly to isolate the reservoir from the pressure waves created when the ram impacts the plunger. It is also an object of the present invention to provide a jet injector system which can use existing pre-filled cartridges. Yet another object of the present invention is to provide a high workload injector that draws a fluid medicament directly from a multi-dose vial.

Another object of the present invention is to provide an accurate and simple to use control mechanism to deliver predetermined amounts of a medication. Yet another object of the present invention is to provide a fluid medicament jet injector with a separate reservoir, which is relatively simple to manufacture, is relatively easy to use, and is comparatively cost effective.

SUMMARY OF THE INVENTION

A jet injector assembly for injecting a fluid medicament into a patient includes a cassette device which interconnects a jet injector to a medicament reservoir. In detail, the device has an upper body and a lower body attached to the upper body to form a fluid pathway at the interface between the upper body and the lower body. The fluid pathway has a first opening and a second opening. The reservoir is attached to the upper body of the device at the first opening of the fluid pathway. A spike extends from the upper body of the device and into the reservoir. This spike is formed with a longitudinal channel and is hollow to establish fluid communication between the reservoir and the fluid pathway.

A pre-filled cartridge, which has a rubber stopper at a lower end, and a rubber plunger at an upper end, is placed in the reservoir. The rubber stopper of the cartridge is pierced by the spike. As a result, the fluid medicament flows from the reservoir through the channel in the spike along the fluid pathway and into the impulse chamber.

Further in detail, the device is formed with an impulse chamber that extends between the upper body to the lower body. A nozzle formed with a tip extends from the lower body of the device to establish fluid communication between the impulse chamber and an orifice in the tip. The fluid medicament is forced from the impulse chamber through the nozzle, and reaches the skin at the orifice in the tip. Also formed in the lower body is a vacuum which forms an interface between the skin of a patient and the cassette. The vacuum surrounds the tip and creates suction between the device and the skin in preparation for an injection.

Jet injectors, in general, require an energy source, or an impulse generator. In operation, a ram extends from the impulse generator and fits into a plunger formed in the impulse chamber. To initiate an injection, the impulse generator uses stored energy to accelerate the ram, which then strikes the plunger. The resultant pressure causes the fluid medicament to be ejected at a high velocity, puncturing the skin of a patient.

It can be appreciated that the pressure required to puncture the skin and initiate an injection has heretofore precluded the use of glass vials and pre-filled cartridges. This is so because, as seen in the present invention, the impulse created by the ram as it impacts the plunger in the impulse chamber creates pressure waves. These waves flow through the fluid pathway back to the reservoir. Large amplitude pressure waves can crack or damage glass vials and pre-filled cartridges in the reservoir. The device of the present invention, however, is designed to attenuate these pressure waves so that glass cartridges and vials can be used in the reservoir without breakage.

As envisioned by the present invention, the fluid medicament in the reservoir is hydraulically protected from the pressure waves by impeding the fluid pathway in several ways. In a preferred embodiment, a tortuous fluid pathway is created between the impulse chamber and the reservoir. This pathway can be formed with curves or right angles to divert the pressure waves in order to protect the glass container in the reservoir from damage. Other aspects for accomplishing this same attenuation include inter alia: a one-way valve or increased resistance, such as would be caused by a reduced diameter in the fluid pathway.

The operation of the jet injector with reservoir requires a coordinated two stage injection. In the first stage the skin is punctured, then during the second stage the fluid medicament is delivered by a delivery mechanism. The delivery mechanism slowly dispenses a measured amount of a fluid medicament from the reservoir through the impulse chamber and the nozzle to the tip. Fluid medicament flows through the tip and into the tissue of the patient at the orifice.

To complete the second stage of the injection, the present invention further envisions control elements which measure and release the fluid medicament from the reservoir. When a full dose cartridge is being used, both the impulse and delivery forces are applied to the cassette plunger and both stages of the injection can be accomplished by the same mechanism. In this case, the complete amount of the fluid medicament to be injected is transferred from the cartridge in the reservoir to the impulse chamber. In one embodiment, a manual mechanism, such as a thumb wheel and screw-ratchet is used to release the medicament from the cartridge. A single spring or gas powered force mechanism can then be employed as the impulse generator, to inject the medication.

Often, however, only a partial dose is to be released from the reservoir. In this case, once the volume to be dispensed is determined, a compressed spring moves the plunger driver to a mechanical stop at a distance corresponding to the volume of the fluid medicament to be administered. Embodiments of the present invention advance the plunger mechanically, electrically, or manually.

Another embodiment of the present invention includes a tubing set for delivering multiple doses of the fluid medicament from one vial. The tubing is attached to the vial at one end and to the reservoir at the other end. The tubing can be reused for many doses. A press-fit luer taper fitting replaces the spike or needle used to puncture the pre-filled cartridge, and attaches the tubing to the cassette upper body. In order to deliver the dose accurately, the present invention envisions a pump mechanism, which shuts off the flow of medication through the tubing. An important consideration when multiple doses are contemplated is the issue of contamination. The present invention therefore envisions replaceable components. Examples of the replaceable parts are the nozzle and tip portions, as well as the cassette/skin interface. Filters are likewise envisioned to shield components from contamination.

In another aspect of the present invention, the device and system of the present invention can be used to establish a methodical, two-step sequence for the injection and infusion of a fluid medicament to a patient. This methodology includes, first, engaging a reservoir in fluid communication with a body member that is formed with a fluid pathway having a first opening and a second opening. As envisioned by the present invention, the reservoir is preferably a vial, a pre-filled cartridge, or some other vessel containing the medicament that is to be infused into the patient. Most likely, the reservoir container will be made of glass. With this structure, the reservoir is engaged with the first opening of the fluid pathway.

An important detail of the present invention is that the body member has an impulse chamber in fluid communication with the second opening of the pathway. Further, as mentioned above, the system of the present invention also includes an impulse generator. Structurally, this impulse generator has a plunger that is slidably positioned on the body member for advancement into the impulse chamber. The impulse generator also includes a ram for selectively striking the plunger to generate a spiked fluid pressure on fluid medicament in the impulse chamber. Finally, the system and device of the present invention includes the nozzle, also mentioned above, that is connected to the body member in fluid communication with the fluid pathway of the body member, through the impulse chamber.

In the operation of present invention, after the reservoir has been engaged in fluid communication with the body member, a partial dose of the fluid medicament is transferred from the reservoir, through the pathway and into the impulse chamber. This leaves a remainder dose of the medicament in the reservoir. As contemplated for the present invention, the partial dose in the impulse chamber will have a fluid volume that is preferably about five to ten microliters and in a range between about one and twenty microliters (1–20 μl). Further, in most instances, the remainder dose that stays in the reservoir will have a fluid volume that is at least two times greater than the fluid volume of the partial dose.

After the partial dose has been transferred into the impulse chamber, the impulse generator is activated to inject the partial dose of fluid medicament from the impulse chamber and through the nozzle, into the patient. This injection is done at a first (spiked) fluid pressure for the purpose of creating a hole in the skin of the patient. This then will allow for the subsequent infusion of the remainder dose. Accordingly, after the partial dose has been injected at the first fluid pressure, the remainder dose from the reservoir is infused through the nozzle and into the patient at a second fluid pressure. For purposes of the present invention the first fluid pressure is greater than the second fluid pressure and, preferably, is at least five times greater than the second fluid pressure. The consequence of this is that the injection of the partial dose from the impulse chamber, and the infusion of the remainder dose from the reservoir are accomplished sequentially to provide for a substantially continuous flow of fluid medicament to the patient.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
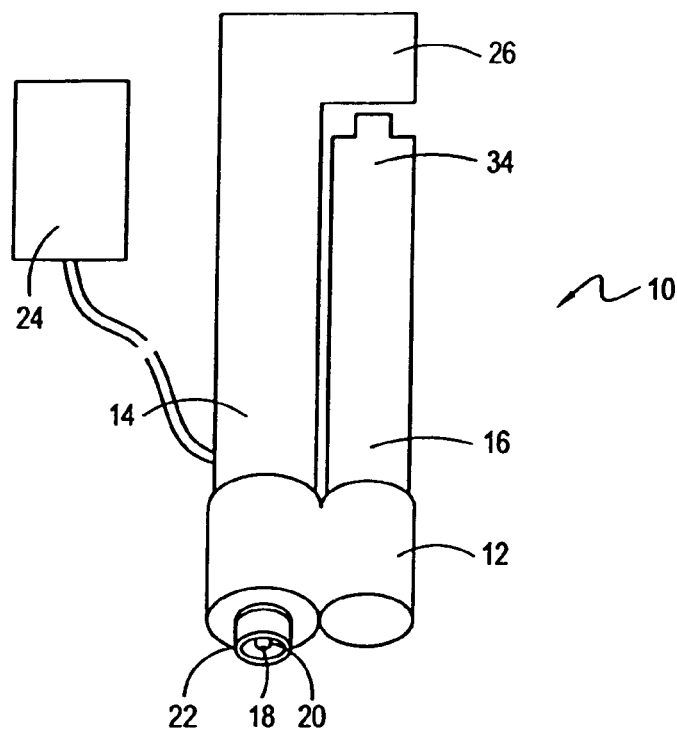
FIG. 1 is a perspective side view of the jet injector system with separate reservoir of the present invention.

A needless jet injector system with a separate reservoir for injecting a fluid medicament into the tissue of a patient in accordance with the present invention is represented in FIG. 1, and is generally designated 10. The system 10 includes a cassette device 12 which connects the jet injector 14 with the reservoir 16. An orifice 18 is formed in a tip 20, which is part of the cassette 12. An interface is created between the skin of a patient and the cassette 12 by a cassette/skin interface 22 formed in the cassette 12, and surrounding the tip 20. A control mechanism 26 is incorporated into the system 10 and interacts with the jet injector 14 and the reservoir 16 at an upper end 34 of the reservoir 16 to release a measured amount of a fluid medicament.

Figure 2:
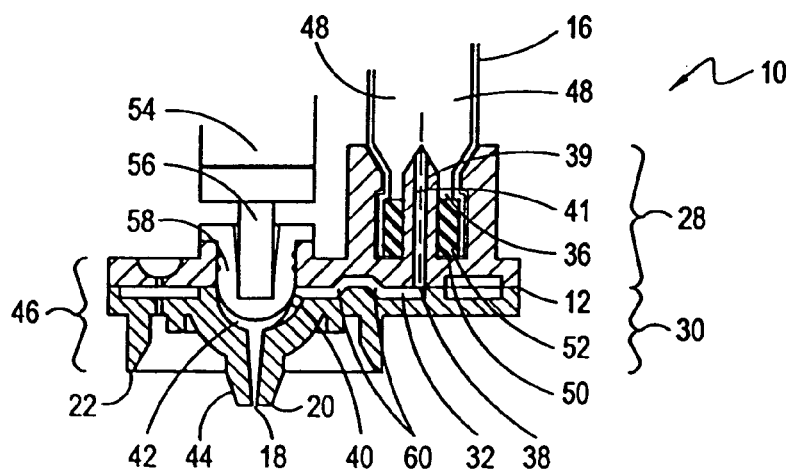
FIG. 2 is an elevational cross sectional view of a cassette and key injector interfaces as would be seen in the plane of FIG. 1, specifically showing the tortuous fluid path of the preferred embodiment.

Referring to FIG. 2, it can be seen that the cassette 12 has an upper body 28 and a lower body 30. A fluid pathway 32 is formed at the interface between the upper body 28 and the lower body 30. The reservoir 16 also has a lower end 36, and attaches at the lower end 36 to the upper body 28. It can also be seen that the fluid pathway 32 leads from an opening 38 at the lower end 36 of the reservoir 16 to an opening 40 in an impulse chamber 42. A spike 39 extends upward from the upper body 28 and into the reservoir 16 through the opening 38 at the lower end 36 of the reservoir 16. This spike 39 is formed with a longitudinal channel 41 which leads to the fluid pathway 32. A pre-filled cartridge 48 which has a rubber stopper 50 at a lower end 52, is placed in the reservoir 16. The rubber stopper 50 is pierced by the spike 39. As a result, the fluid medicament flows from the reservoir 16, through the channel 41 in the spike 39, along the fluid pathway 32, and into the impulse chamber 42. It can also be seen in FIG. 2 that the impulse chamber 42 is formed in the cassette 12, and extends from the upper body 28 to the lower body 30. The lower body of the cassette 30 further forms a nozzle 44 that extends from the impulse chamber 42 and ends at the orifice 18 in the tip 20. By cross referencing FIG. 2 with FIG. 1, it can be understood that the lower body 30 forms the cassette/skin interface 22. A vacuum system 46 creates suction between the cassette 12 and the skin of the patient at the interface 22, stabilizing the skin in preparation for an injection.

By further cross referencing FIG. 1 and FIG. 2, it can be appreciated that the jet injector 14 also requires an impulse generator 54 to supply the energy needed to force a fluid medicament through the skin. In operation, as shown in FIG. 2, a ram 56 extends from the impulse generator 54 and fits into a plunger 58 formed in the impulse chamber 42. To initiate an injection, the impulse generator 54, using stored energy, accelerates the ram 56, which strikes the plunger 58. The fluid medicament in the impulse chamber 42 is forced from the impulse chamber 42 through the nozzle 44 to the orifice 18 at the tip 20 and punctures the skin of the patient. It can be understood that the pressure created by the ram 56 as it impacts the plunger 58 creates pressure waves. These waves flow back through the fluid pathway 32 to the reservoir 16. Because large amplitude pressure waves can damage the pre-filled cartridge 48, the system 10 of the present invention is designed to attenuate these pressure waves. FIG. 2 illustrates a preferred embodiment of a fluid pathway 32 which will attenuate the pressure waves. A tortuous fluid pathway 32 is formed with several right angles 60 between the reservoir 16 and the impulse chamber 42 to divert the pressure waves.

Figure 3:
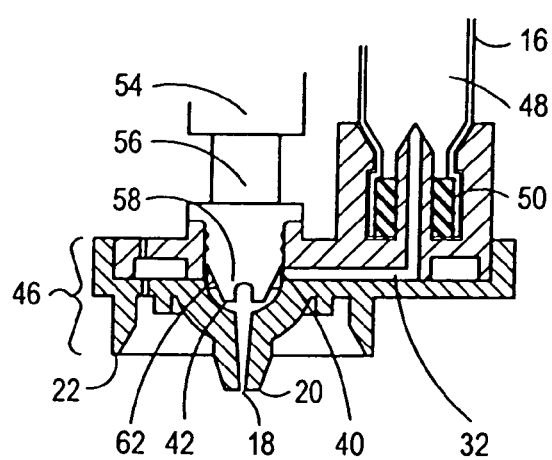
FIGS. 3, 4, 5 and 6 are elevational cross sectional views of cassettes, as would be seen in the plane of FIG. 1, showing a number of means for attenuating pressure waves leading to the source of the fluid medicament.

Referring to FIG. 3, another embodiment includes a flap 62 formed on the plunger 58. This flap 62 extends below the opening 40 of the fluid pathway 32 into the impulse chamber 42 when the plunger 58 is impacted by the ram 56. As a result, the fluid pathway 32 is blocked when pressure is exerted on the plunger 58.

Figure 4:
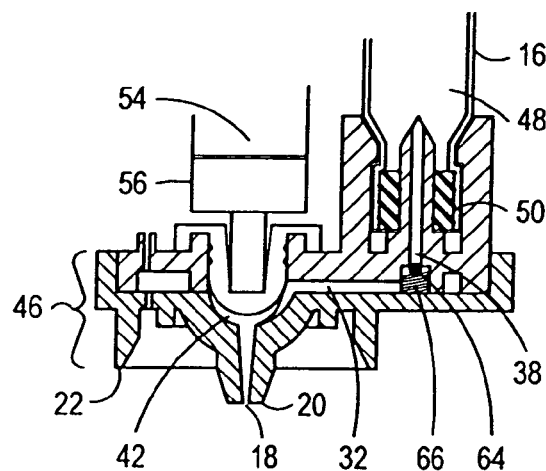

FIG. 4 shows an embodiment using a ball check valve 64 attached to a spring 66 which closes the opening 38 of the reservoir 16 in response to pressure exerted along the fluid pathway 32.

Figure 5:
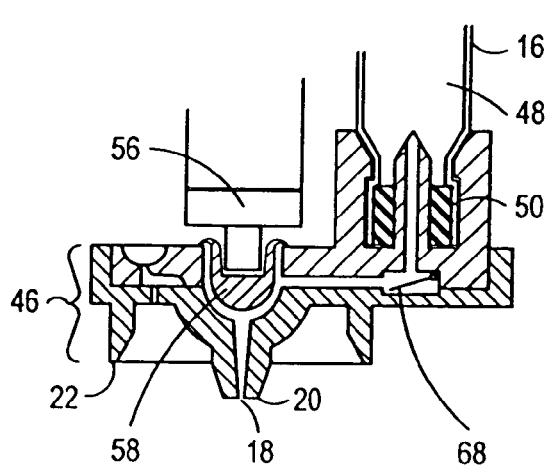

FIG. 5 shows yet another embodiment with a flap valve 68 which isolates the reservoir 16 from the pressure waves created by the impact of the ram 56 on the plunger 58.

Figure 6:
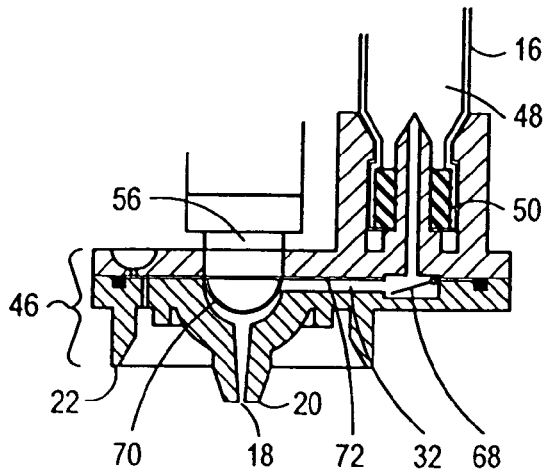

FIG. 6 illustrates another embodiment in which the flap valve 68 and an elastomeric diaphragm 70 are molded of one piece. This embodiment includes a ridge 72 in the elastomeric material which surrounds the fluid pathway 32. The ridge 72 would be compressed by the pressure waves, sealing the fluid pathway 32.

Figure 7:
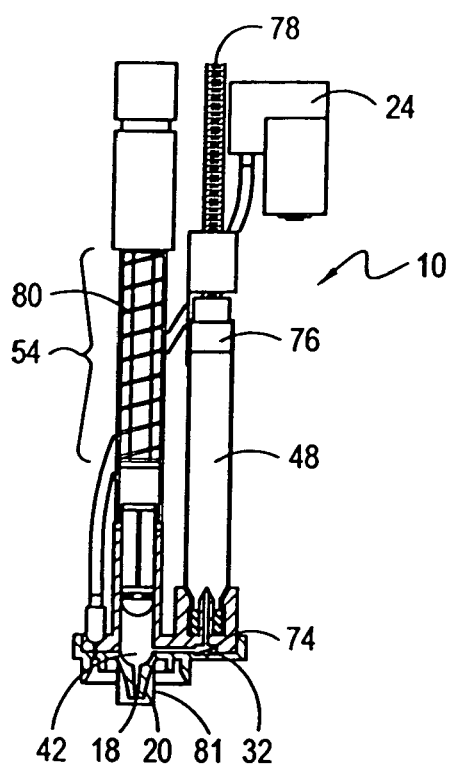
FIG. 7 is an elevational cross sectional view as would be seen along the plane of FIG. 1, of an injection system based on transferring the complete dose to be injected to a cassette chamber.

Referring to FIG. 7, a system 10 for administering a full dose cartridge 48 shows the complete amount of the fluid medicament to be delivered in the impulse chamber 42. In this embodiment, a valve 74 closes the fluid pathway 32. A movable stopper 76 is also shown, which is advanced by a lead screw 78. A single spring 80 is employed as the impulse generator 54 to inject the medication. It can be appreciated that a replaceable cap 81 is used to cover the tip 20 when the system 10 is not in use. Cross referencing FIG. 7 with FIG. 1 also shows the vacuum source 24.

Figure 8:
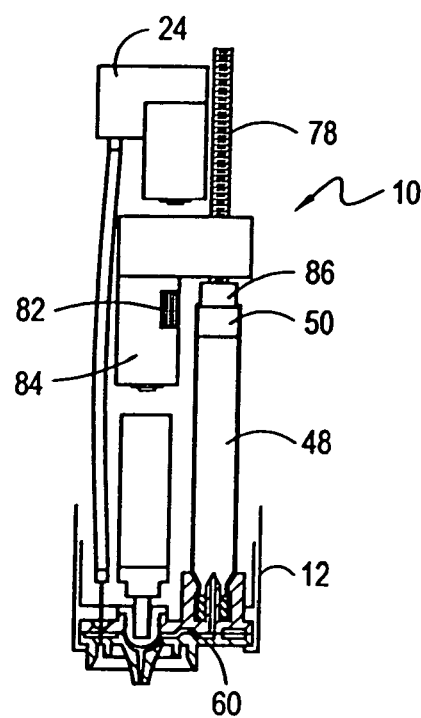
FIG. 8 is an elevational cross sectional view as would be seen along the plane of FIG. 1, of an injection system with an electrically powered subsystem for a partial-dose cassette.

FIG. 8 shows an embodiment of the system 10 in which an encoder 82 is attached to a motor 84. The motor 84 advances the lead screw 78 to determine the amount of medication to be dispensed from the cartridge 48. The encoder 82 indicates when a driver 86 has advanced a rubber stopper 50 of the cartridge 48 the proper distance.

Figure 9:
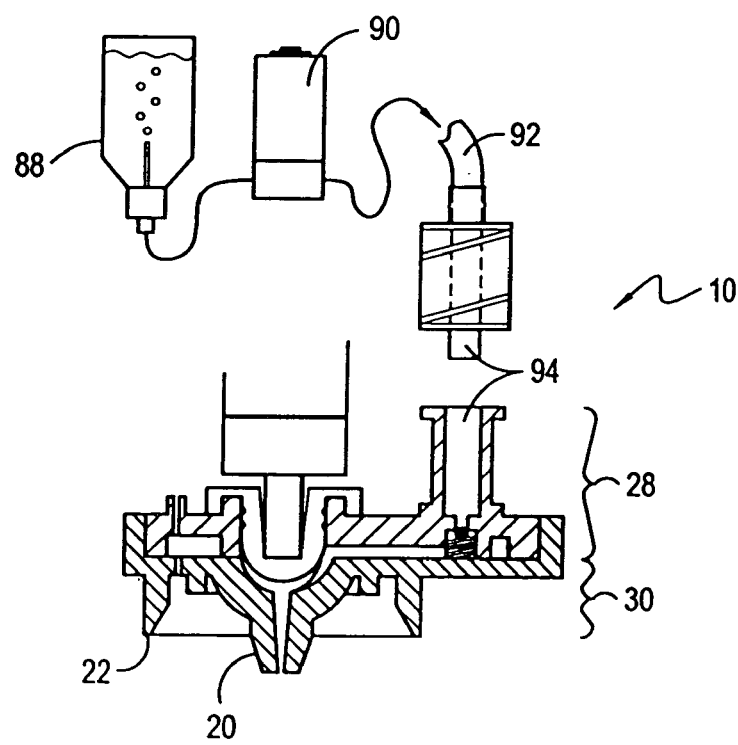
FIG. 9 is an elevational cross sectional view as would be seen in the plane of FIG. 1, of a cassette with a replaceable tip for use with a multi-dose vial.

FIG. 9 shows the system 10 being used with a multi-dose vial 88. A pump 90 is attached to tubing 92 which in turn attaches to the multi-dose vial 88 and to the upper body 28. Luer attachments 94 securely fasten the tubing 92 to the upper body 28. The pump 90 shuts off the flow of medication through the tubing 92, determining the amount of medication to be injected. Replaceable components of the lower body 30 are also illustrated. These include the tip 20 and the cassette/skin interface 22.

In an operation of the present invention, a fluid medicament is injected and infused into a patient (not shown) in a sequential two-step process. The sequence of events in this process, or method, are schematically shown in FIGS. 10A, 10B, 10C and 10D. Specifically, beginning with FIG. 10A, a body member 28/30 (a combination of the upper body 28 and lower body 30 disclosed above) is shown formed with a fluid pathway 32 that extends through the body member 28/30, between an opening 38 and an opening 40. A spike 39, that is structured to be in fluid communication with the opening 38 of fluid pathway 32, is also shown to be part of the body member 28/30. Further, the nozzle (tip) 20 is formed on body member 28/30 to be in fluid communication with the opening 40 of fluid pathway 32.

Figure 10A:
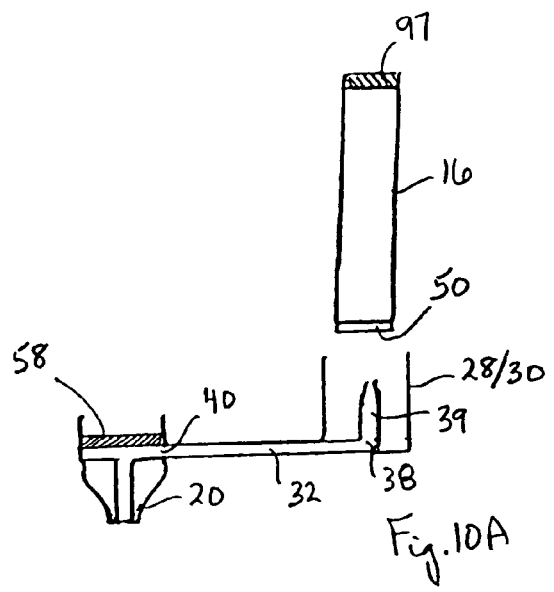
FIG. 10A is a schematic drawing of a system of the present invention before engagement of a reservoir with a body member.
Figure 10B:
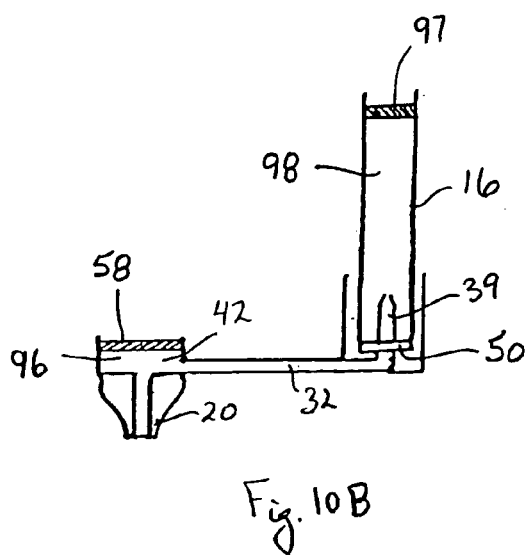
FIG. 10B is a schematic drawing of the system shown in FIG. 10A after engagement of the reservoir with the body member, and after a partial dose of medicament has been drawn from the reservoir.
Figure 10C:
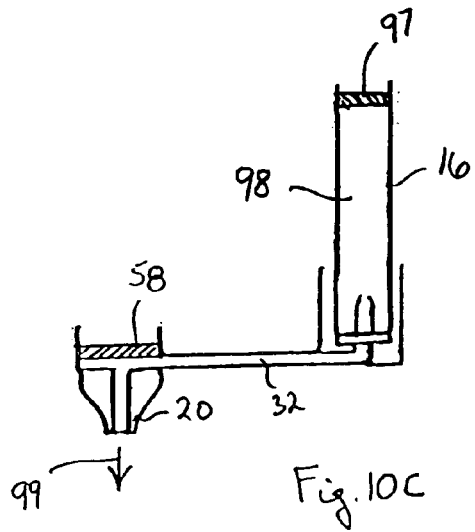
FIG. 10C is a schematic drawing of the system shown in FIG. 10B after the partial dose has been injected into a patient.
Figure 10D:
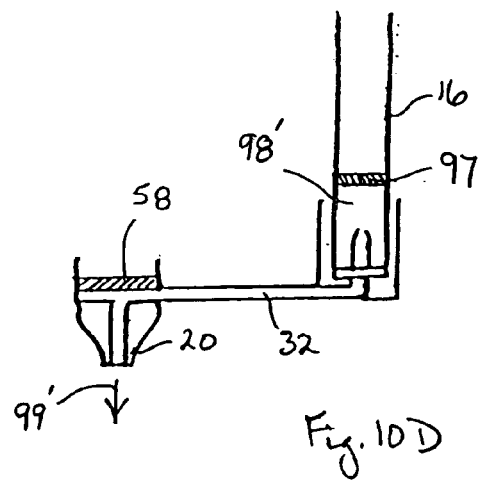
FIG. 10D is a schematic drawing of the system shown in FIG. 10B after at least part of a remainder dose has been infused into the patient.

When the reservoir 16 is engaged with the body member 28/30, the spike 39 penetrates through the stopper 50 to establish fluid communication between the reservoir 16 and the fluid pathway 32 of body member 28/30. Once this engagement has been accomplished, the plunger 58 can be withdrawn from the nozzle (tip) 20 to create an impulse chamber 42 (see FIG. 10B). As this is done, a partial dose 96 of fluid medicament is transferred from the reservoir 16, and through the fluid pathway 32, into the impulse chamber 42. This also leaves a remainder dose 98 of the fluid medicament in the reservoir 16. As intended for the present invention, the partial dose 96 will be generally in a range of one to twenty microliters. Further, the remainder dose 98 will be generally more than twice the volume size of the partial dose 96 and, in some instances, may be much more. For example, as contemplated for the present invention, the reservoir 16 may include several doses for subsequent infusion to the same patient, or others. In any event, when system 10 is in the configuration shown in FIG. 10B, it is ready for the two-step sequential operation that includes: first an injection step (FIG. 10C); and second, an infusion step (FIG. 10D). Typically, the injection step and infusion step will be accomplished sequentially to provide for a substantially continuous flow of fluid medicament to the patient. As a practical matter, however, there may be a slight delay (e.g. one half of a second) between the injection and infusion steps.

For the injection step, the plunger 58 is rapidly advanced into the impulse chamber 42 by the impulse generator 54 (see FIGS. 2–4). The consequence of this is that the partial dose 96 is rapidly expelled through the nozzle (tip) 20 in the direction of arrow 99 for injection into the patient. The fluid pressure that is generated on partial dose 96 in the impulse chamber 42 by this action is short lived and is spiked. For the purposes of the present invention, the purpose of this injection step is to create a hole in the skin of the patient through which a subsequent infusion of the remainder dose 98 can be accomplished. Accordingly, after the injection step it is important there still be a patent fluid passageway that extends from the reservoir 16, through the fluid pathway 32 and out through the tip (nozzle) 20.

As shown in FIG. 10D, the infusion step is completed after the injection step (FIG. 10C), and results in the infusion of a remainder dose 98 into the patient in the direction of 99'. This infusion is caused by advancing the plunger 97 into the reservoir 16, and may be accomplished in any manner well known in the art. As indicated above, an additional remainder dose(s) 98' may still be in the reservoir 16 after the infusion of the intended remainder dose 98 has been accomplished. Importantly, the fluid pressure used for this infusion is less than the pressure used in the injection step. Specifically, this is possible because the infusion can be made over an extended period of time and the entry hole through the skin of the patient has already been made. As intended for the present invention, the injection pressure will typically be around five times greater than the infusion pressure. An important benefit of this difference is that the reservoir 16 may be made of glass or any other material suitable for storing a fluid medicament.

While the particular Sequential Impulse/Delivery Fluid Medicament Injector as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown.

What is claimed is:

1. A method for infusing a fluid medicament into a patient which comprises the steps of:

engaging a reservoir in fluid communication with a body member, wherein the reservoir is filled with the fluid medicament and the body member is formed with a fluid pathway having a first opening and a second opening, and further wherein the reservoir is engaged with the first opening of the fluid pathway;

establishing fluid communication between an impulse chamber having a nozzle and the second opening of the pathway;

transferring a partial dose of the fluid medicament from the reservoir, through the pathway and into the impulse chamber to leave a remainder dose in the reservoir;

using a first plunger in said impulse chamber to inject the partial dose of fluid medicament from said impulse chamber through the nozzle and into the patient at a first fluid pressure; and advancing a second plunger into the reservoir to infuse the remainder dose from the reservoir through the nozzle and into the patient at a second fluid pressure, wherein said first fluid pressure is greater than said second fluid pressure.

2. A method as recited in claim 1 wherein the partial dose has a fluid volume in a range between one and twenty microliters (1–20 µl), and further wherein the remainder dose has a fluid volume at least two times greater than a fluid volume for the partial dose.

3. A method as recited in claim 1 wherein the reservoir is made of glass and the reservoir is selected from a group consisting of a vial and a pre-filled cartridge.

4. A method as recited in claim 1 wherein the first fluid pressure is at least five times greater than the second fluid pressure.

5. A method as recited in claim 1 wherein said using step is accomplished using an impulse generator which comprises a ram for striking said first plunger to generate the first fluid pressure on the partial dose.

6. A method as recited in claim 1 wherein said using step and said advancing step are accomplished sequentially to provide for a substantially continuous flow of fluid medicament to the patient.

7. A method for infusing a fluid medicament into a patient which comprises the steps of:

engaging a reservoir in fluid communication with a body member, wherein the reservoir is filled with the fluid medicament and the body member is formed with a fluid pathway having a first opening and a second opening, and further wherein the reservoir is engaged with the first opening of the fluid pathway;

establishing fluid communication between an impulse chamber and the second opening of the pathway;

transferring a partial dose of the fluid medicament from the reservoir, through the pathway and into the impulse chamber to leave a remainder dose in the reservoir;

using a first plunger to inject the partial dose of fluid medicament from the impulse chamber through a nozzle and into the patient at a first fluid pressure; and advancing a second plunger to infuse the remainder dose from the reservoir through the nozzle and into the patient at a second fluid pressure, wherein said first fluid pressure is greater than said second fluid pressure, and wherein said using step and said advancing step are accomplished sequentially to provide for a substantially, uninterrupted flow of fluid medicament to the patient.

8. A method as recited in claim 7 wherein the remainder dose has a fluid volume at least two times greater than a fluid volume for the partial dose, and wherein the first fluid pressure is at least five times greater than the second fluid pressure.

9. A method as recited in claim 7 wherein said using step is accomplished using an impulse generator which comprises a ram for striking said first plunger to advance said first plunger into the impulse chamber to generate the first fluid pressure on the partial dose.

10. A device for infusing a fluid medicament into a patient which comprises:

means for engaging a reservoir in fluid communication with a body member, wherein the reservoir is filled with the fluid medicament and the body member is formed with a fluid pathway having a first opening and a second opening, and further wherein the reservoir is engaged with the first opening of the fluid pathway;

means for establishing fluid communication between an impulse chamber and the second opening of the pathway;

means for drawing a partial dose of the fluid medicament from the reservoir, through the pathway and into the impulse chamber to leave a remainder dose in the reservoir;

means for using a first plunger to inject the partial dose of fluid medicament from said impulse chamber through a nozzle and into the patient at a first fluid pressure; and means for advancing a second plunger to infuse the remainder dose from the reservoir through the nozzle and into the patient at a second fluid pressure, wherein said first fluid pressure is greater than said second fluid pressure, and wherein said using means and said advancing means are sequentially operated to provide for a substantially continuous flow of fluid medicament to the patient.

11. A device as recited in claim 10 wherein the remainder dose has a fluid volume at least two times greater than a fluid volume for the partial dose, and wherein the first fluid pressure is at least five times greater than the second fluid pressure.

12. A device as recited in claim 10 wherein the reservoir is made of glass.

13. A device as recited in claim 10 wherein said using means is an impulse generator which comprises a plunger slidably positioned for advancement into the impulse chamber; and a ram for striking said first plunger to advance said first plunger into the impulse chamber to generate the first fluid pressure on the partial dose.

14. A device as recited in claim 10 wherein the reservoir is formed with a stopper and said engaging means is a spike, and further wherein the spike pierces the stopper to deliver the fluid medicament from the reservoir into the fluid pathway.

15. A device as recited in claim 13 wherein a pressure wave is created when the ram strikes the first plunger, and wherein the device further comprises a means in the fluid pathway for attenuating the pressure wave within the device to protect the reservoir from the pressure wave.

16. A device as recited in claim 15 wherein the fluid pathway, in part, is formed with a relatively small diameter and acts as the pressure attenuating means by creating a fluid flow resistance to delivery of the fluid medicament from the reservoir into the fluid pathway.

17. A device as recited in claim 15 wherein the attenuating means is the fluid pathway formed with a plurality of angles between the reservoir and the impulse chamber for creating a tortuous pathway.

18. A device as recited in claim 15 wherein the attenuating means is a one-way valve.

19. A device as recited in claim 10 further comprising a suction means for creating a vacuum between the skin of the patient and the nozzle to stabilize the skin against the nozzle during an injection of the fluid medication into the patient.

* * * * *